United States Patent
Flower et al.

(10) Patent No.: US 6,678,555 B2
(45) Date of Patent: Jan. 13, 2004

(54) CIRCUITS FOR INCREASING THE RELIABILITY OF AN IONTOPHORETIC SYSTEM

(75) Inventors: Ronald J. Flower, Atlanta, GA (US); Kenneth E. Garde, New Windsor, NY (US); Steven D. Walter, Vernon, NJ (US)

(73) Assignee: Vyteris, Inc., Fair Lawn, NJ (US)

( * ) Notice: Subject to any disclaimer, the term of this patent is extended or adjusted under 35 U.S.C. 154(b) by 0 days.

(21) Appl. No.: 10/127,333

(22) Filed: Apr. 22, 2002

(65) Prior Publication Data

US 2003/0067358 A1 Apr. 10, 2003

Related U.S. Application Data

(62) Division of application No. 09/315,768, filed on May 20, 1999, now Pat. No. 6,385,488.

(51) Int. Cl.$^7$ .................................... A61N 1/30
(52) U.S. Cl. ........................ 604/20; 324/433
(58) Field of Search ................ 604/20–21, 501; 324/433, 426; 607/29

(56) References Cited

U.S. PATENT DOCUMENTS

| | | | |
|---|---|---|---|
| 4,141,359 A | | 2/1979 | Jacobsen et al. |
| 4,406,658 A | * | 9/1983 | Lattin et al. .................. 604/20 |
| H516 H | * | 9/1988 | Lattin et al. .................. 604/20 |
| 4,808,152 A | | 2/1989 | Sibalis |
| 4,839,597 A | * | 6/1989 | Rowland .................... 324/433 |
| 4,942,883 A | | 7/1990 | Newman |
| 5,042,975 A | * | 8/1991 | Chien et al. .................. 604/20 |
| 5,047,007 A | | 9/1991 | McNichols et al. |
| 5,069,211 A | * | 12/1991 | Bartelt et al. ................ 607/74 |
| 5,135,478 A | | 8/1992 | Sibalis |
| 5,224,928 A | | 7/1993 | Sibalis et al. |
| 5,246,418 A | | 9/1993 | Haynes et al. |
| 5,254,081 A | | 10/1993 | Maurer et al. |
| 5,306,235 A | | 4/1994 | Haynes |
| 5,314,502 A | | 5/1994 | McNichols et al. |
| 5,421,817 A | * | 6/1995 | Liss et al. ..................... 604/20 |
| 5,444,378 A | * | 8/1995 | Rogers ........................ 324/428 |
| 5,499,967 A | | 3/1996 | Teillaud et al. |
| 5,562,607 A | | 10/1996 | Gyory |
| 5,645,526 A | | 7/1997 | Flower |
| 5,688,232 A | | 11/1997 | Flower |
| 5,693,024 A | | 12/1997 | Flower |
| 5,830,175 A | | 11/1998 | Flower |
| 5,857,994 A | | 1/1999 | Flower |
| 5,876,368 A | | 3/1999 | Flower |
| 5,899,876 A | | 5/1999 | Flower |
| 5,961,482 A | * | 10/1999 | Chien et al. ................. 604/20 |
| 5,978,701 A | | 11/1999 | Johnson et al. |
| 5,991,655 A | | 11/1999 | Gross et al. |
| 6,009,344 A | * | 12/1999 | Flower et al. ................ 604/20 |

(List continued on next page.)

FOREIGN PATENT DOCUMENTS

| | | |
|---|---|---|
| AU | 52260/98 | 5/1998 |
| CA | 2230813 | 3/1997 |
| CA | 2233067 | 4/1997 |
| CA | 2233068 | 4/1997 |
| DE | 40 28 125 A1 | 7/1991 |
| EP | 0 092 015 A1 | 10/1983 |
| EP | 0 461 680 A2 | 12/1991 |
| GB | 2 064 178 A | 6/1981 |
| WO | WO 96/22124 A | 7/1996 |
| WO | WO 97/07854 | 3/1997 |
| WO | WO 97/11743 | 4/1997 |

*Primary Examiner*—Mark Bockelman
(74) *Attorney, Agent, or Firm*—Kirkpatrick & Lockhart LLP

(57) ABSTRACT

Circuits are provided for increasing the reliability of an iontophoretic drug delivery system. Such circuits detect the failure of a crystal oscillator of the system, the failure of a voltage reference of the system, or the impending failure of a battery power source of the system.

1 Claim, 12 Drawing Sheets

U.S. PATENT DOCUMENTS

| | | | |
|---|---|---|---|
| 6,018,680 A | | 1/2000 | Flower |
| 6,029,083 A | * | 2/2000 | Flower et al. ................. 604/20 |
| 6,035,234 A | | 3/2000 | Riddle et al. |
| 6,049,210 A | * | 4/2000 | Hwang ....................... 324/428 |
| 6,090,095 A | | 7/2000 | McNichols et al. |
| 6,167,301 A | | 12/2000 | Flower et al. |
| 6,208,891 B1 | | 3/2001 | Flower |

* cited by examiner

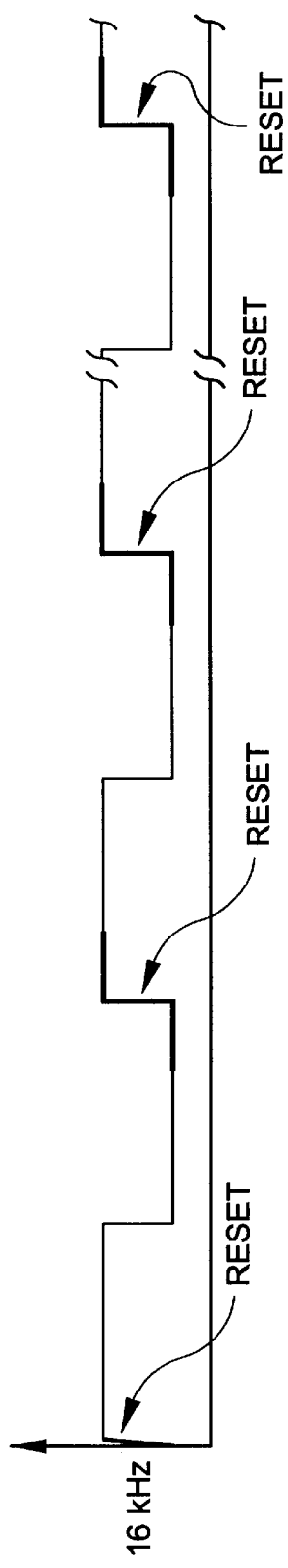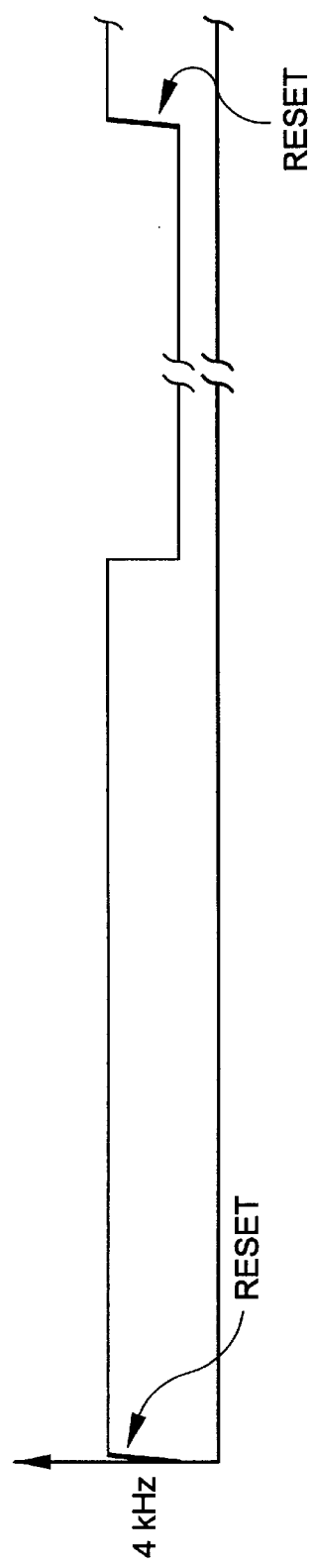
FIG-5C
FIG-5D

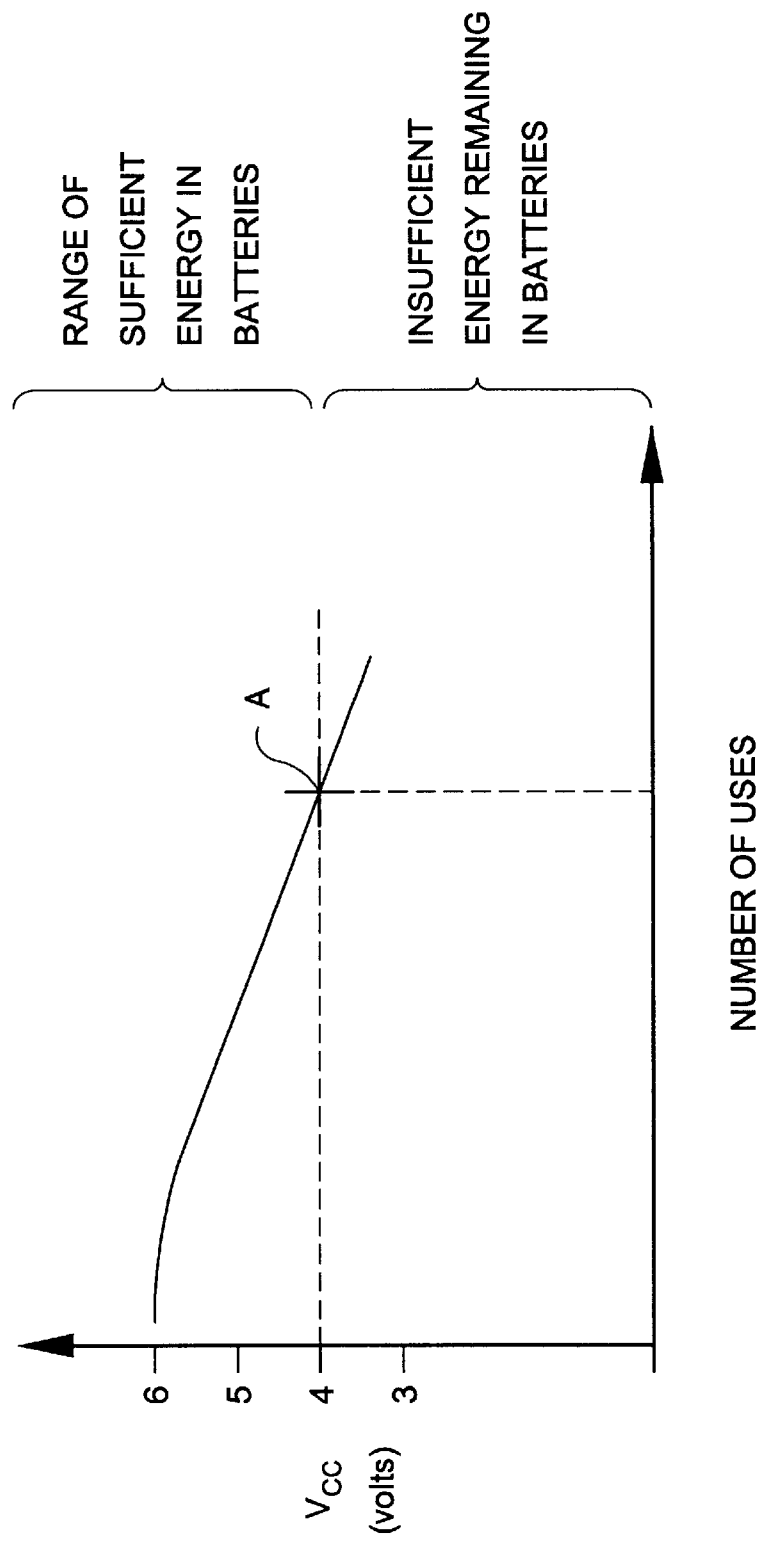

CIRCUITS FOR INCREASING THE RELIABILITY OF AN IONTOPHORETIC SYSTEM

CROSS REFERENCE TO RELATED APPLICATIONS

This is a divisional of copending U.S. patent application Ser. No. 09/315,768, filed on May 20, 1999 now U.S. Pat. No. 6,385,488.

BACKGROUND OF THE INVENTION

1. Field of the Invention

The invention is in the field of iontophoresis. In particular, the invention relates to circuits for increasing the reliability of an iontophoretic drug delivery system.

2. Description of Related Art

Iontophoresis is the migration of ions when an electrical current is passed through a solution containing an ionized species, usually the ionic form of a drug or other therapeutic agent (hereinafter referred to as the "drug"). One particularly advantageous application of iontophoresis is the noninvasive transdermal delivery of ionized drugs into a patient using low levels of current. Iontophoretic drug delivery offers an alternative and effective method of drug delivery over other methods such as passive transdermal patches, needle injection, and oral ingestion, and is an especially effective method for children, the bedridden and the elderly. Known advantages of transdermal delivery include avoiding the risks and inconvenience of intravenous delivery. Also, problems associated with oral drug ingestion, such as drug loss caused by digestion and hepatic first pass metabolism are avoided as the gastrointestinal tract and liver (on first pass) are bypassed. Transdermal delivery advantageously provides continuous drug delivery, easy termination and more convenience.

An iontophoresis transdermal drug delivery system usually includes a patch having multiple reservoirs, one of which, called the active reservoir, contains positively- or negatively-charged drug ions, and another one of which, called the return reservoir, contains an electrolytic solution, such as a saline solution. Located within the reservoirs are electrodes for applying current into the patch. The iontophoresis system also includes a controller device, which is electrically and mechanically connected to the patch. The controller usually contains a power source such as a battery, as well as electrical circuitry required for generating and regulating the current applied to the patch electrodes.

One possible configuration of an iontophoretic delivery device is shown in FIG. 1. A controller 80, including a battery, is respectively connected to an anode 61 and cathode 62 in the patch 60 via the electrical interconnectors 11 and 12. The anode 61 is arranged in the active reservoir containing a positively-charged drug, while the cathode 62 is arranged in the return reservoir containing the electrolytic (or saline) solution. If the drug is negatively-charged, the anode and cathode arrangement in the reservoirs is reversed, so that when current is applied to the electrodes, drug ions will be repelled from the reservoir of similar polarity. When the patch 60 is placed on the skin of a user and the controller applies current to the patch 60, the charged drug is forced into the skin of the patient. Other ions are returned to the return reservoir as the body completes the ionic circuit. For example, if the drug is negatively-charged, a AgCl cathode will repel them through the skin, while positively-charged sodium ions are attracted to the cathode. At the same time, negatively-charge chlorine ions will flow from the skin into a return reservoir containing saline toward the anode.

The controller usually includes a microprocessor or state machine to implement numerous control functions. For example, a microprocessor executes software programs which, inter alia, command the current generation and regulation circuitry to provide the required amount of current over a period of time. Because the amount of drug delivered to the patient is directly proportional to the amount of current delivered, the drug dosage can be controlled by regulating the amount of current delivered to the patch.

The microprocessor or the state machine is clocked externally by a counter driven by a crystal oscillator having, for example, a 32.768 kHz frequency (i.e., a watch crystal). This permits the microprocessor or state machine, and thus the system, to cycle through current delivery states, each state defining the current to be delivered over a predetermined time interval. For example, curve A of FIG. 2 shows a desired current delivery profile. In this profile, the current starts at zero amps. After a first time, $t_1$, the current rises to a first current level, after a second time, $t_2$, rises to a second, higher current level, after a third time, $t_3$, drops back to the first current level, and after a fourth time, $t_4$, drops back to zero amps. When the crystal oscillator is operating properly, the microprocessor cycles through each of those current delivery levels over the course of the delivery cycle, thereby directing the current circuitry to generate and deliver the correct amount of current to the patch in accordance with each current level.

However, if the oscillator becomes inoperable during the course of a drug delivery cycle, a drug overdosage or underdosage condition may arise. For example, in curve B of FIG. 2, the oscillator has failed at time $t_b$. At this time, the microprocessor (or state machine) will become stuck at its last program instruction (or step), that is, the instruction that causes the current circuitry to generate and deliver the second, higher level of current. Accordingly, when the oscillator fails at time $t_b$, the system will continue to provide the higher level of current beyond time $t_3$, since the microprocessor (or state machine) cannot reach the next program instruction (or step), and thus the next current state. This may result in an inaccurate amount of delivered drug. In the case of curve B, this would be a drug overdosage. In contrast, as shown by curve C, the oscillator has stopped at time $t_a$. This failure causes the microprocessor (or state machine) not to reach the instruction (or step) corresponding to the higher current level time interval. Instead, current continues to be delivered at the lower current level, which may result in a drug underdosage or overdosage, depending on when the current is caused to stop.

In addition, the iontophoretic system may employ a voltage reference to provide a highly-accurate output voltage, for example, 1.203 volts, to critical components within the current circuitry. In particular, one way of generating the patch current is to output a digital value from the microprocessor (or state machine) to a D/A converter. The D/A converter in turn converts the digital value to an analog voltage, based on the voltage reference output voltage. That analog voltage is then converted to the patch current using a voltage-to-current converter. An inaccurate voltage reference output voltage, however, will cause both the analog voltage and thus the patch current to be inaccurate. An inaccuracy in patch current may result in a drug overdosage condition, if the patch current is too high, or a drug underdosage condition, if the patch current is too low.

Furthermore, a drug underdosage condition may result if the system's battery power source runs out during a drug delivery cycle. The running down of the battery energy will first cause too little patch current to be produced, and eventually the failure of the device circuitry and no patch current.

SUMMARY OF THE INVENTION

It is thus an object of the present invention to provide circuits for increasing the reliability of an iontophoretic drug delivery system to minimize the possibility of drug overdosage or underdosage conditions.

In one aspect of the present invention, circuits are provided to detect the failure of a crystal oscillator of the system.

In another aspect of the present invention, circuits are provided to detect the failure of a voltage reference of the system.

In yet another aspect of the present invention, a circuit is provided to detect the impending failure of a battery power source of the system.

BRIEF DESCRIPTION OF THE DRAWINGS

These and other features and advantages of the present invention can be best understood by reference to the detailed description of the preferred embodiments set forth below taken with the drawings, in which:

FIGS. 5A–5F are signals corresponding to the circuit of FIG. 4.

FIG. 9 shows battery voltage discharge as the number of completed iontophoretic deliveries increase.

DETAILED DESCRIPTION OF THE PREFERRED EMBODIMENTS

Figure 1:
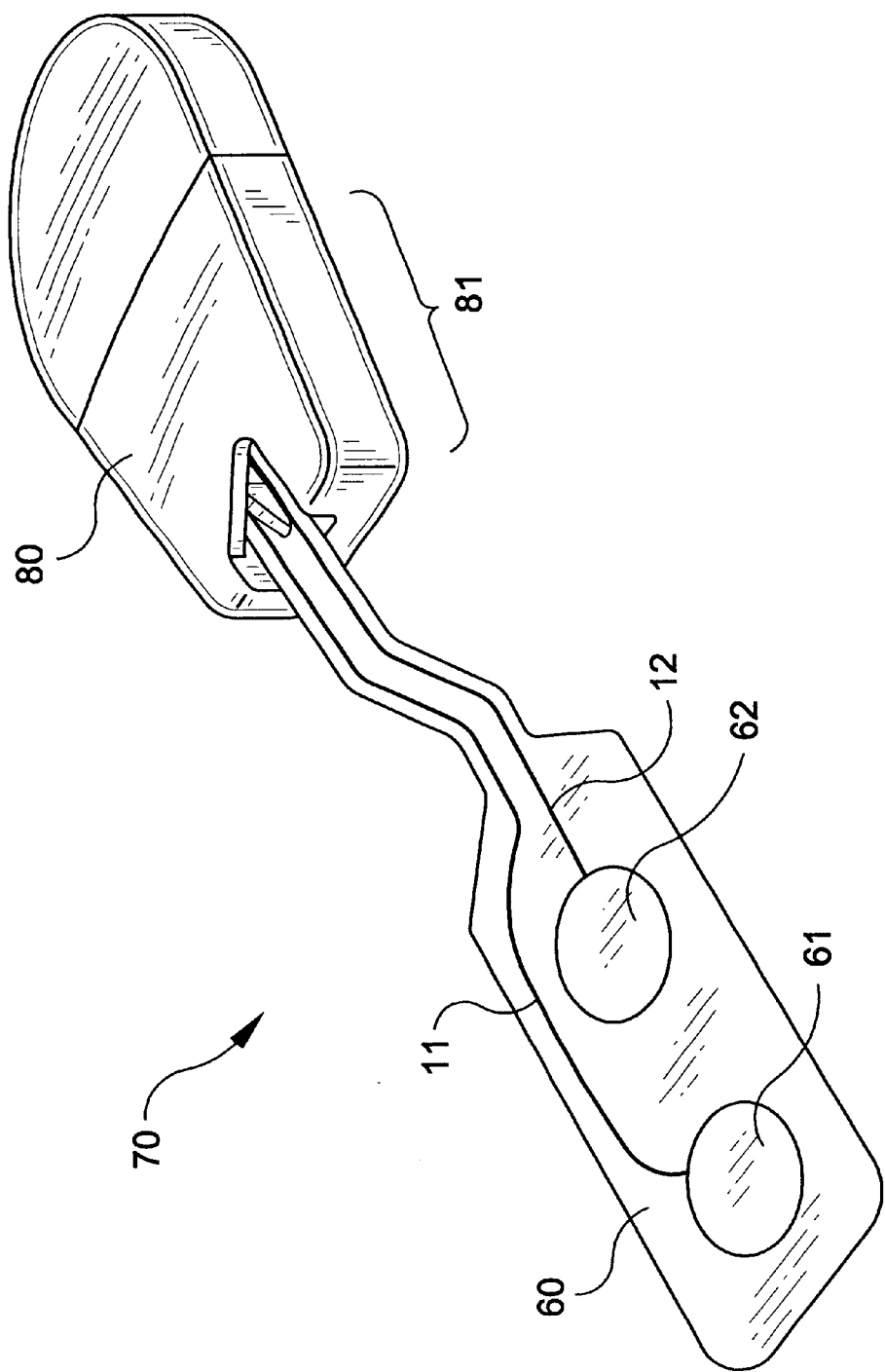
FIG. 1 is a perspective view of an iontophoretic system that includes a patch and a controller.
Figure 2:
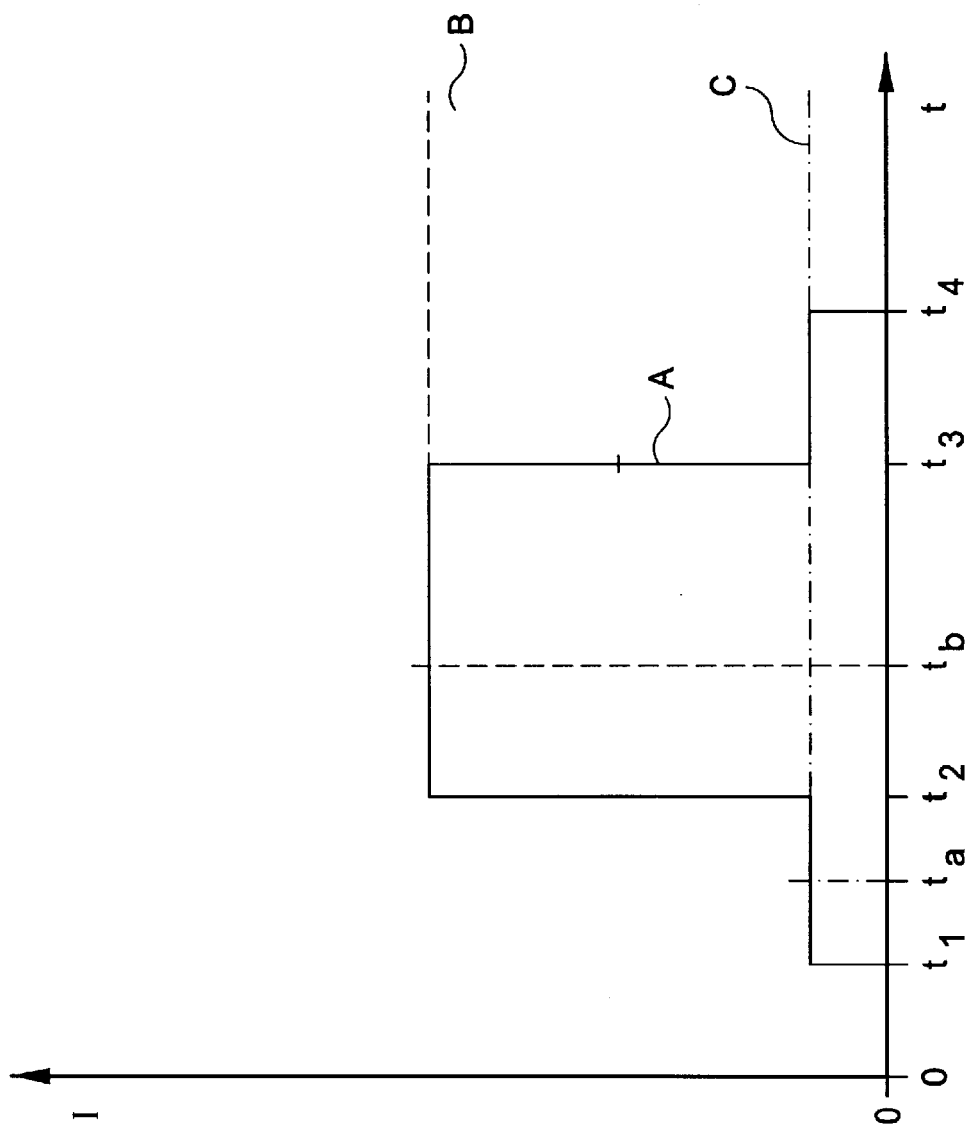
FIG. 2 is an example of a current profile (A) when the crystal oscillator has been operable throughout the drug delivery cycle, and current profiles (B and C) when the crystal oscillator has failed at various points of time during the drug delivery cycle.
Figure 3:
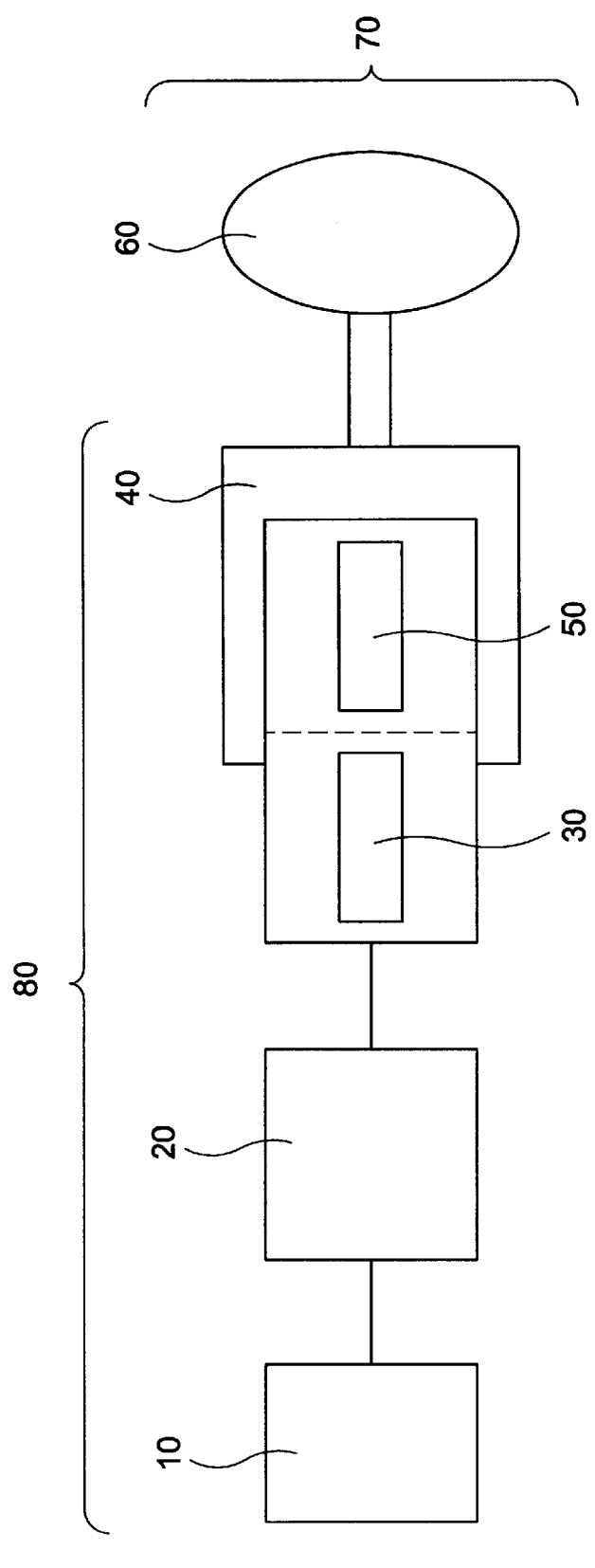
FIG. 3 is an overview of an iontophoretic system and its controller circuitry.

The embodiments of the present invention relate to an iontophoretic system 70 including a patch 60 and a controller 80, as illustrated in FIGS. 1 and 3. As shown in FIG. 1, the controller 80 includes an outer casing 81 which houses the power source (such as, but not limited to, a battery) and current generation and regulation circuitry required for driving current into the patch 60. The casing of the controller 80 may be made of a plastic, metal or other suitable material for encasing and protecting the current regulating circuitry. The patch electrodes 61 and 62 electrically connect to the current controller 80 via electrical interconnectors 11 and 12.

As shown in more detail in FIG. 3, the controller 80 includes a microprocessor 20, which upon execution of software, generates commands to control the various functions of the controller, including but not limited to generating and regulating the current applied to the patch as dictated by a predetermined current delivery profile. To accomplish these functions, the microprocessor 20 is connected to the current generation and regulation circuitry, including digital interface and control circuit 30, analog current control circuit 50 and peripheral current control circuitry 40. The peripheral current control circuitry 40 applies the current to the patch 60. The microprocessor 20, digital interface 30, and analog control circuitry 50, together with a memory 10 described in detail below, comprise an application specific integrated circuit (ASIC). The peripheral current control circuitry 40 is called "peripheral" because it is outside the ASIC. Of course, it will be appreciated that the current generation and regulation circuitry may take on other configurations, and need not be implemented by an ASIC.

The microprocessor 20 is also connected to at least one memory 10 such as random access memory (RAM) or a read-only memory (ROM), in which are stored the current delivery profiles. The controller software may also be stored in the same memory or a separate memory (not shown). The memory 10 may store, for example, each current delivery profile as rate of change of current, or current steps, and the time after start-up at which those current steps are to occur. The microprocessor reads the current delivery profile information to generate the appropriately timed commands required to cause the current generation and regulation circuitry to deliver the amount of current dictated by the profile information. In essence, the microprocessor may cycle through the current profile information until the time after start-up matches one of the stored times. At that time, the microprocessor outputs the desired current level, as a digital value, associated with that time to the digital interface of the current circuitry. The digital interface, which includes a digital to analog convertor, converts the digital value to an analog voltage, which will be that voltage required to produce the current level at that point in time of the current delivery profile. The D/A convertor outputs the analog voltage to a voltage-to-current conversion circuit, which generates the required patch current. Feedback from a current sense resistor may be used to control this patch current more precisely.

As described above in the background section, the crystal oscillator, voltage reference or battery may fail during the operation of the drug delivery device, and those failures may undesirably lead to a drug overdosage or underdosage condition. The embodiments of the present invention described below allow for the detection of those failures, thus minimizing the possibility of undesirable misdosages.

Figure 4:
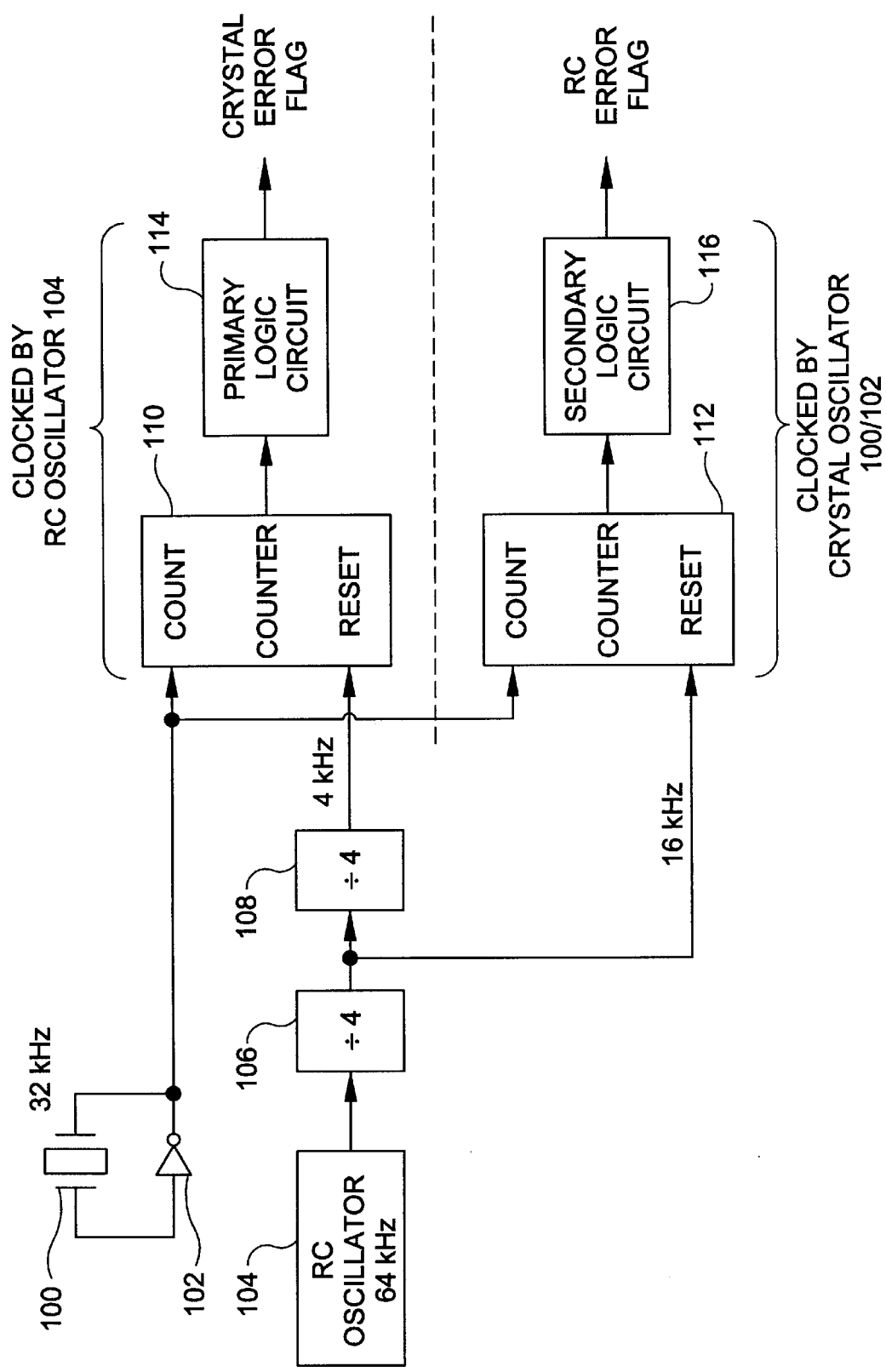
FIG. 4 is a circuit for detecting the failure of a crystal oscillator in accordance with one embodiment of the present invention.

In the first embodiment of the present invention, as shown in FIG. 4, a second, independent time base, using different technology than the crystal oscillator time base, is provided to detect a failure of the crystal oscillator. The failure may be that the crystal oscillator has ceased to operate totally, or that the crystal is running unacceptably too fast or too slow. The second, independent time base, however, may also fail, and thus the circuit in FIG. 4 also detects the failure of the second time base, as described in more detail below.

In FIG. 4, a crystal 100 having a frequency of approximately 32 kHz is connected to an inverter 102 to form a crystal oscillator, the output of which is a 32 kHz square wave. The crystal oscillator output is input to a count input of a counter 110 and to a count input of a counter 112. The circuit of FIG. 4 also employs a resistor-capacitor (RC)

oscillator circuit 104 having a frequency of approximately 64 kHz, which is divided by 4 to 16 kHz by divider circuit 106 and again divided by 4 to 4 kHz by divider circuit 108. The implementation of a RC oscillator circuit 104 is well known by those skilled in the art.

Figure 5A:
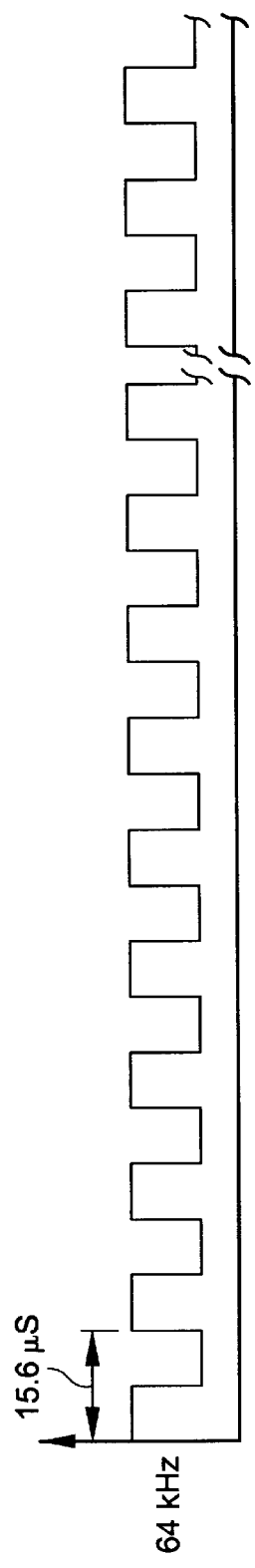
Figure 5B:
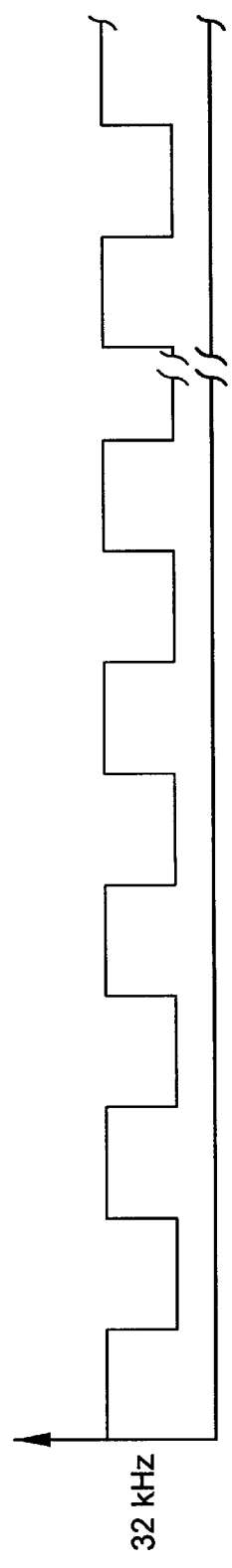
Figure 5E:
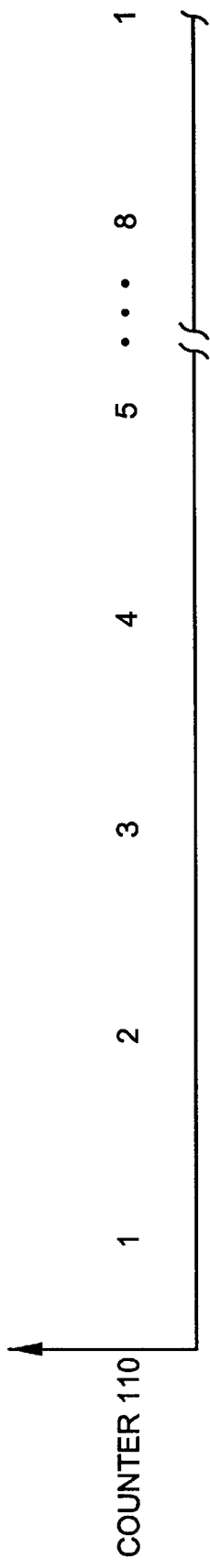
Figure 5F:
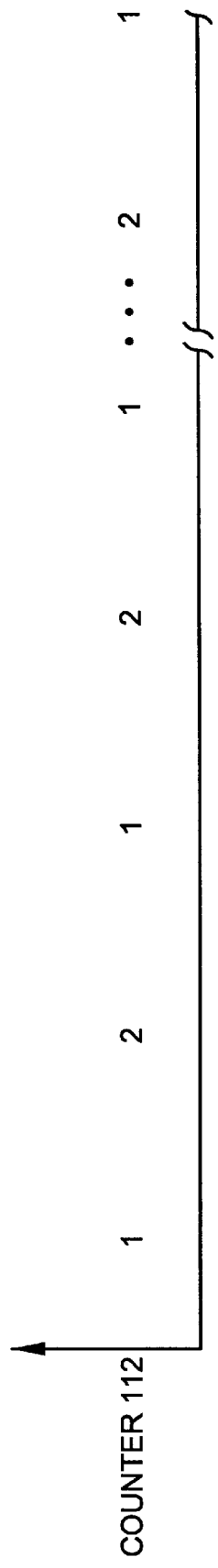

The counter 110 is clocked by the 64 kHz RC oscillator output shown in FIG. 5A, and thus the counter 110 increments by one for every cycle of the 32 kHz crystal oscillator output, as shown in FIGS. 5B and 5E. Meanwhile, the counter 112 is clocked by the 32 kHz crystal oscillator output shown in FIG. 5B, and thus the counter 112 increments by one for every cycle of the 32 kHz crystal oscillator output, as shown in FIG. 5F. The 4 kHz RC clock signal, shown in FIG. 5D, drives the reset input of the counter 110, while the 16 kHz RC clock signal, shown in FIG. 5C, drives the reset input of the counter 112. Thus, when the crystal and RC oscillators are operating normally, counter 110 counts to eight before resetting, while counter 112 counts only to two before resetting, as respectively shown in FIGS. 5E and 5F. The output count of counter 110 is input to primary logic circuit 114 to determine if the crystal has failed, and the output count of counter 112 is input to secondary logic circuit 116 to determine if the RC oscillator has failed. The primary logic circuit 114 is also clocked by the 64 kHz RC oscillator, while the secondary logic circuit is clocked by the 32 kHz crystal oscillator.

If the crystal oscillator has stopped running, the following occurs. First, the counter 112 and secondary logic circuit 116 are no longer being clocked and are thus non-operational. The counter 110, however, is clocked by the RC oscillator and is thus still operational, but will stop counting because the crystal has stopped. The primary logic circuit 114 is also operational because it too is clocked by the RC oscillator. The counter 110 will eventually reset to zero on the rising edge of the 4 kHz clock and will remain at zero due to the failure of the crystal. This "remain at zero" condition of counter 110 can be easily detected by the primary logic circuit (as described below). The primary logic circuit 114 will then output a crystal error flag of "one" indicating that the crystal oscillator has failed.

Further, even if the crystal has not completely failed, it nonetheless may be operating much too fast or too slow, that is, beyond a certain predetermined acceptable frequency. In this event, the counter 110 will still count, but the count will deviate from the normally expected count. The primary logic circuit determines whether the count of counter 110, between two successive resets of the counter 110, is within an acceptable count window. For example, if the count is between 3 and 14 (normally a count of 8 would be expected), then the frequency of the crystal oscillator may be considered acceptable. The size of the count window allows for inaccuracies in the frequency of the RC oscillator, which tends to be less accurate than the crystal oscillator. Of course, the size of the count window can be made smaller, such as from 7 to and including 9, or can even be a single count of 8. If the count of counter 110 between two consecutive resets is determined to be outside the count window, for example less than three or greater than 14, then the primary logic circuit 114 outputs a crystal error flag of one indicating that the crystal has failed. As mentioned above, if the crystal has completely failed, the count between two consecutive resets will be zero, which is also outside the count window (for example, of 3 to 14), and in which case the primary logic circuit 114 outputs a crystal error flag of one.

The RC oscillator may also fail. This condition must also be detected, because a failed RC oscillator can not be used to determine whether the crystal oscillator is operating correctly. In this case, the counter 110 and primary logic circuit 114, both clocked by the RC oscillator circuit 104, no longer operate, while the counter 112 and secondary logic circuit 116, both clocked by the 32 kHz crystal oscillator, continue to operate. Also, the counter 112 does not reset because the 16 kHz reset signal, derived from the (inoperable) RC oscillator, is not forthcoming. Accordingly, the 32 kHz crystal oscillator causes the counter 112 to continue counting beyond 2 counts. When the secondary logic circuit 116 detects that the count of the counter 112 is greater than a detection threshold of 2 counts, it outputs an RC error flag of "one" to indicate that the RC oscillator 104 has failed. Because the RC oscillator 104 may be less accurate than the crystal oscillator, a detection threshold of 3 or more counts, instead of 2 counts, may be used.

When either the crystal error flag or the RC error flag is detected, and if desired latched, then the iontophoretic system can shut down the current circuitry and/or take some other warning action to alert the user that a system failure has occurred. For example, when either flag has been set to "one", the flag may be used to cause an output current control FET to be turned off by pulling its gate low. This will prevent current from being delivered to the patch. Alternatively, or at the same time, a light, sound or buzzer may be set off to warn the user. The user can then take an alternative action to deliver the drug, such as replacing the failed controller with a working controller.

Figure 6:
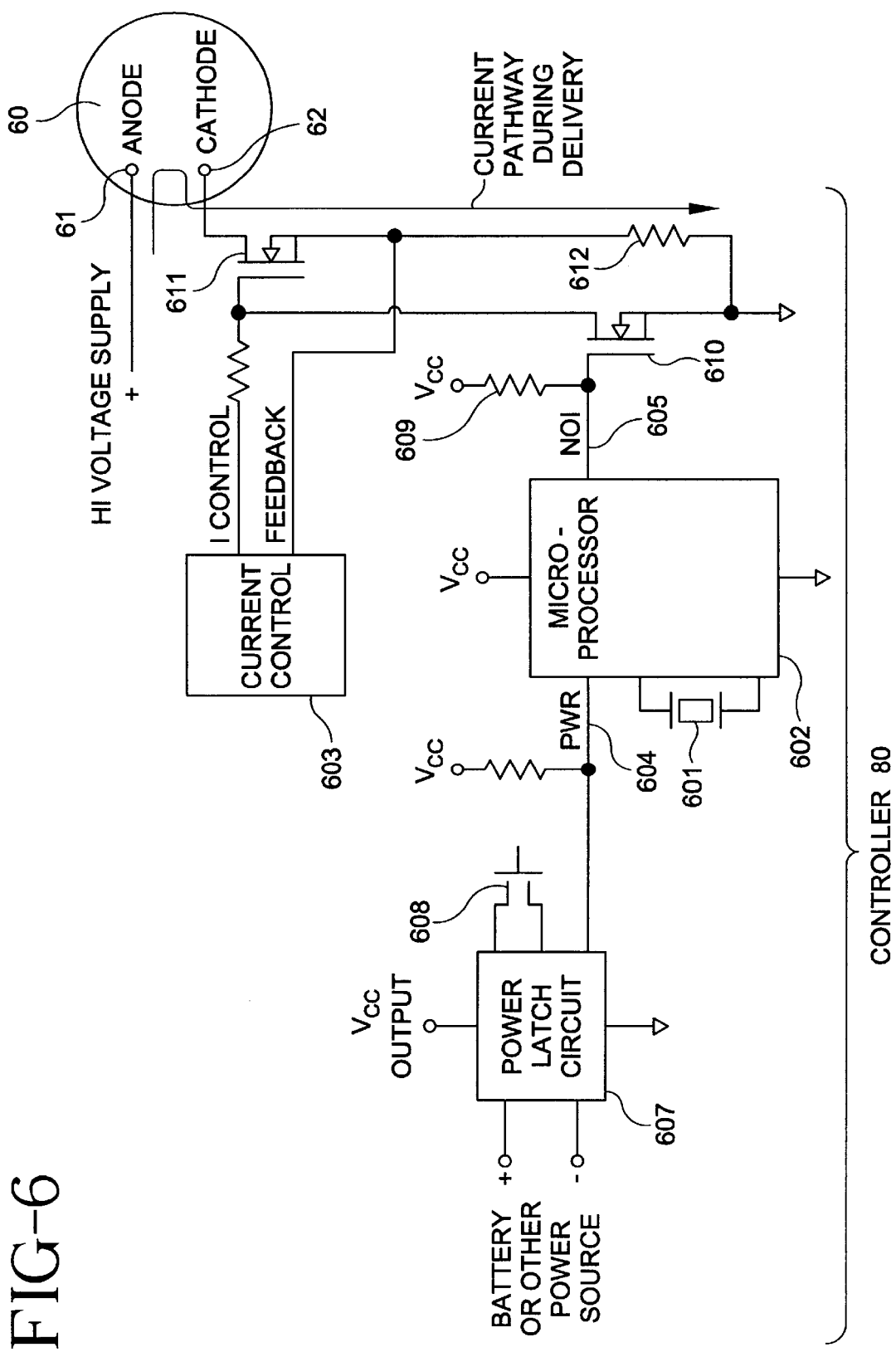
FIG. 6 is a circuit for detecting a crystal oscillator failure in accordance with another embodiment of the present invention.

In a second embodiment of the present invention, shown in FIG. 6, the complete failure of the crystal oscillator 601 will cause the patch current to shutdown, as follows. The microprocessor 602 is chosen for this particular iontophoretic system to have the property that its input/output (i/o) lines default to a hi-impedance (input) state upon power-up. Power (from a battery or other power source, not shown) is supplied to the controller through a power latch circuit 607 that uses a transient input (such as from a normally-open, or NO, button 608 or other triggering mechanism) to latch the power on, thus supplying the rest of the circuitry with voltage $V_{cc}$.

Upon power-up, normally open input (NOI) line 605 is pulled high by $V_{cc}$ through pull-up resistor 609. When NOI line 605 is high, the n-channel MOSFET 610 is on and the gate to the current control FET 611 is low. Therefore the current control FET 611 is OFF and no pathway exists for current delivery through the anode and cathode.

The crystal oscillator 601 allows the microprocessor to start executing pre-programmed soft ware instrictions, including providing current delivery instructions to current control circuit 603. During delivery of current, i.e., an operational state, the microprocessor changes its digital i/o lines from a hi-impedance (input) state into a digital output line, and drives NOI line 605 low. This turns MOSFET 610 off, which in turn allows the current control circuitry 603 to regulate the current from the patch anode 61 to cathode 62 via the current control FET 611. Current level information is fed back to the current control circuitry 603 via its connection to current sense resistor 612.

If the crystal fails totally, no further microprocessor instructions can occur. This causes an internal watchdog timer, clocked by an independent oscillator, in the microprocessor reset the microprocessor upon time-out, i.e., to switch the microprocessor to the reset state. Since the microprocessor is reset, the NOI line is again in a hi-impedance input state. Because of the pull-up resistor 609, MOSFET 610 is turned on, the current control FET 611 is OFF, and current delivery is stopped. Additionally, should a failure occur in the preprogrammed software instructions, the watchdog timer switches the microprocessor from the operational state to the reset state thereby stopping current delivery. Examples of software failures include, but are not limited to, a sequence of events beyond those anticipated in the preprogrammed software instructions, an error in the software instructions that causes an infinite loop and the like.

Figure 7A:
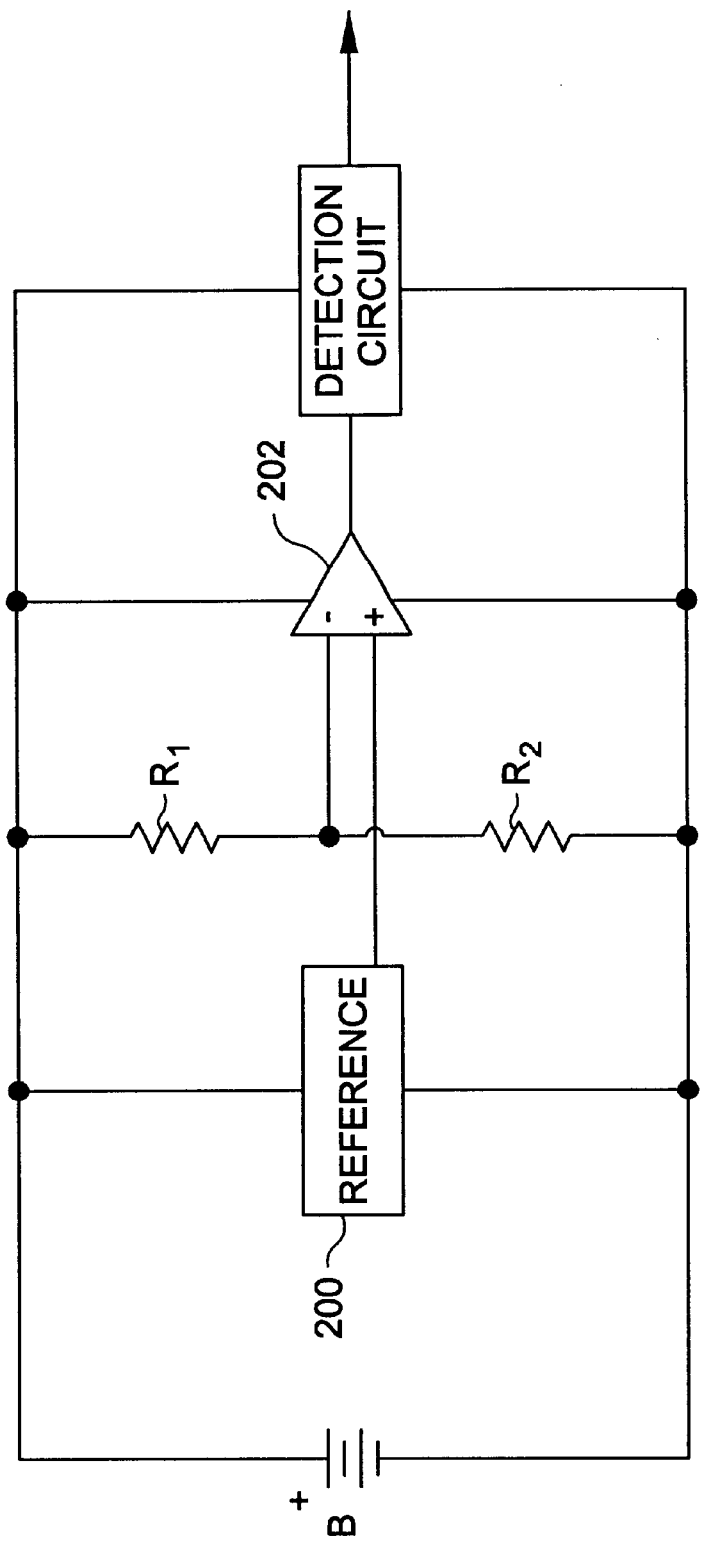
FIGS. 7A and 7B are circuits for detecting a failure of a voltage reference in accordance with yet another two embodiments of the present invention.

In a third embodiment of the present invention, as shown in FIG. 7A, a voltage reference 200 is powered by a battery B. The voltage reference 200 is designed to provide a constant output voltage over a range of battery voltages. For example, the voltage reference 200 may be designed to provide a constant, fixed output voltage of 1.2 volts when the battery is between 1.5 volts and 3.0 volts. The implementation of a voltage reference is well-known in the art and its internal components are not shown. Below a certain battery voltage, for example, 1.5 volts, the reference voltage may become inaccurate, which, as described above, may cause the output current and drug dosage to become inaccurate. To prevent the voltage reference from reaching this point of inaccuracy when the battery loses power, the battery voltage must be detected before it falls below the minimum acceptable battery voltage for the voltage reference circuit, as follows.

The battery B also powers a voltage divider circuit of two resistors R1 and R2. The respective resistances of resistors R1 and R2 are selected to provide a voltage above the reference voltage when the battery is at full operating voltage. For example, R2:R1 may be selected to be 2:1 so that a voltage of 2 volts, which is above the 1.2 volts reference voltage, is provided across R2 when the full battery voltage is 3 volts. The voltage across R2 is input to the negative terminal of a voltage comparator, op amp 202 also powered by battery B, and the output voltage of the voltage reference 200 is input to the positive terminal of the op amp 202. The output of the op amp 202 will be about 0 volts when the battery voltage is full, since the voltage across R2, 2 volts, is greater than the reference voltage of 1.2 volts.

However, when the voltage across R2 drops below the reference voltage, the output of the op amp 202 will swing to almost the battery voltage (approximately, the battery voltage less a few tenths of a volt). This voltage swing in the output of op amp 202 is easily detectable, and may be used to turn off the current generating circuit or trigger a warning action, as described in relation to the first embodiment. For example, when the battery voltage drops from 3.0 volts to 1.7 volts, the voltage across R2 will be about two thirds of 1.7 volts, or about 1.13 volts, which is less than the 1.2 volts reference voltage. The voltage output by the voltage comparator will then swing from 0 volts to about 1.6 volts, which is detected by other logic circuitry (not shown). Thus, the fall of the battery voltage to 1.7 volts is detected and acted upon before the voltage reference circuit is allowed to operate below the minimum acceptable battery voltage (for example, 1.5 volts) and thus generate an inaccurate reference voltage.

Figure 7B:
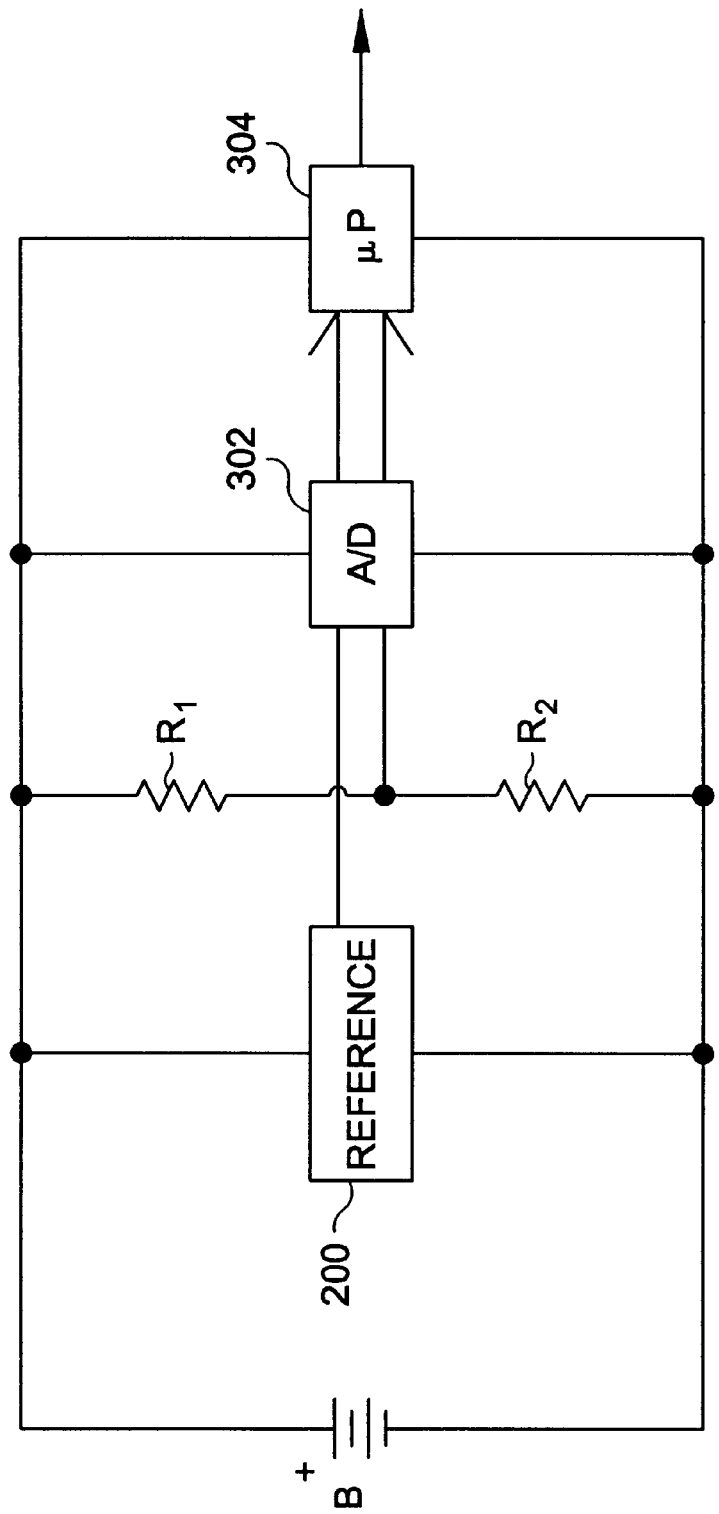

In a fourth embodiment of the present invention, shown in FIG. 7B, the op amp 202 of FIG. 7A is replaced by an analog-to-digital (A/D) converter 302 and microprocessor 304, both of which are powered by the battery B. In this embodiment, the reference voltage and the voltage across R2 are input to one time-multiplexed A/D converter, or two separate A/D converters, the outputs of which in either case are digital values representing the respective voltages. These digital values are input to the microprocessor 304, which in turn compares them to determine whether the battery voltage has dropped to a point where the voltage reference output is unacceptable. By use of the microprocessor, a precise comparison can be made between the reference voltage and voltage across R2, and the detection threshold may be easily adjusted by reprogramming the microprocessor.

In a fifth embodiment of the present invention, a microprocessor 801 is chosen such that it can use one of two voltage sources as a reference for analog to digital conversion to convert analog inputs 805 (current and voltage). The microprocessor may use the supply voltage $V_{cc}$ 803 as a reference, or it may use a voltage $V_{ref}$ 804 generated by independent voltage reference circuitry 802. The choice of reference $V_{cc}$ or $V_{ref}$ is under software control.

For example, the microprocessor can use $V_{ref}$ 804 as an A/D reference voltage during current delivery. In this case, values of 0 volts to $V_{ref}$ volts on an analog line 805 respectively produce digital values of 0 to 255 (counts). If, on the other hand, $V_{cc}$ is selected by the microprocessor to be the A/D reference voltage, values of 0 volts to $V_{cc}$ volts on an analog line 805 respectively produce digital values of 0 to 255 (counts).

In the latter case, the microprocessor can read the $V_{ref}$ line 804 as an analog input. The resulting conversion by the A/D circuitry within the microprocessor will yield a value of 255 (counts)*$(V_{ref}/V_{cc})$. This formula allows the microprocessor to determine the voltage of the batteries indirectly. It is advantageous to ensure that sufficient battery energy is available for an iontophoretic drug delivery cycle prior to the start of that delivery. For example, if $V_{cc}$ changes from 6 volts to 3.5 volts as the device is used, a point A on the battery discharge curve (FIG. 9) can be chosen (for example, 4.0 volts) so that the microprocessor does not initiate a drug delivery cycle because the battery may have insufficient energy to complete that drug delivery cycle.

Figure 8:
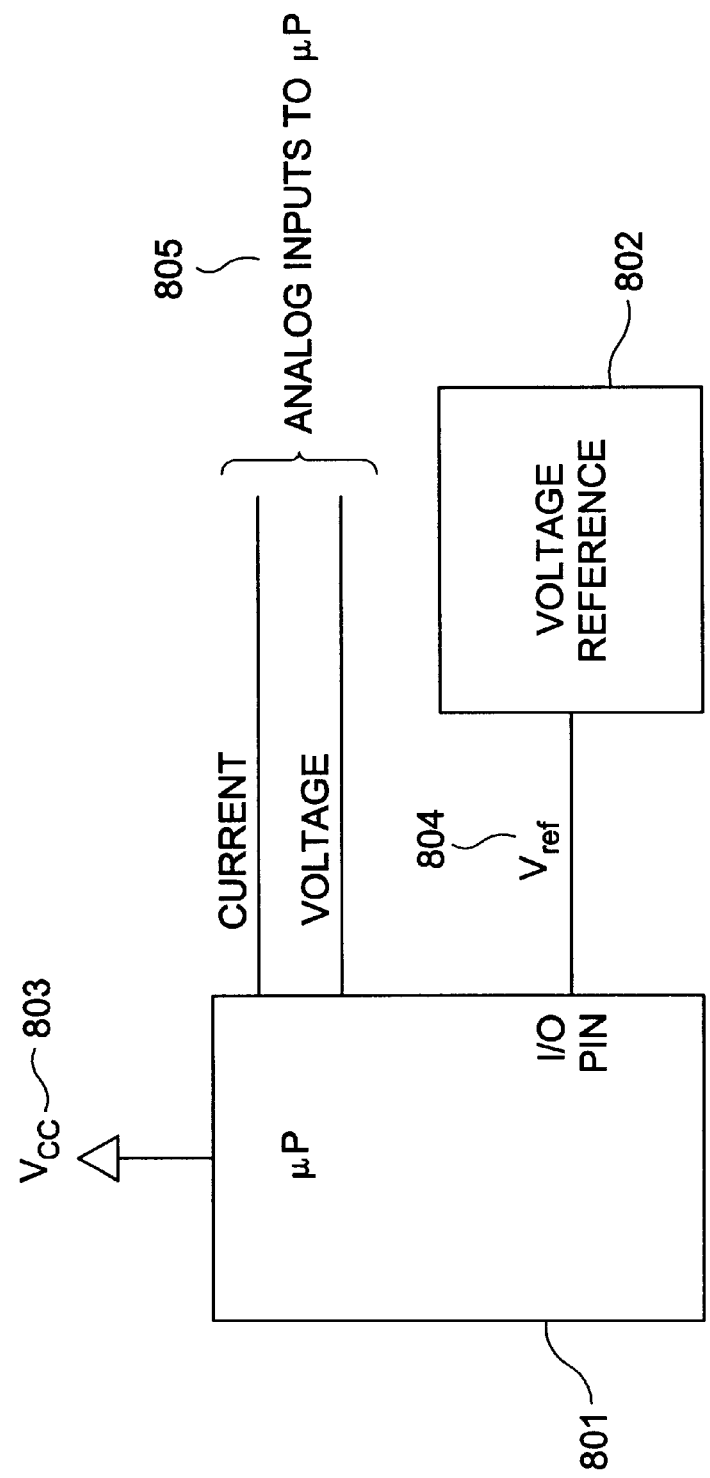
FIG. 8 is a diagram of the inputs to a microprocessor (software implementation) for battery energy detection in accordance with yet another embodiment of the is present invention.

For example, referring to FIG. 8, if $V_{ref}$ is 3.5 volts, the microprocessor reads the $V_{ref}$ line 804 when the batteries are fresh ($V_{cc}$=6 volts). The value obtained by the above formula is:

255 counts*(3.5 volts/6.0 volts)=148 counts

Table 1 below shows the A/D value when the microprocessor reads the $V_{ref}$ line 804 as $V_{cc}$ decreases from 6.0 volts to 3.9 volts.

TABLE 1

| $V_{ref}$ | $V_{cc}$ | Count |
|---|---|---|
| 3.5 volts | 6.0 volts | 148 |
| 3.5 volts | 5.0 volts | 178 |
| 3.5 volts | 4.0 volts | 223 |
| 3.5 volts | 3.9 volts | 228 |

For this example, the arbitrary threshold of 4.0 volts is chosen as that voltage $V_{cc}$ below which too little battery energy remains to perform one last delivery cycle. The software reads $V_{ref}$ as an analog input and compares the A/D value thereof against 223 counts corresponding to 4.0 volt threshold. If the A/D value is above 223, the voltage $V_{cc}$ is too low. If the value is equal to or below 223, there is enough energy in the batteries for one more iontophoretic delivery cycle. In this manner the software can prevent partial drug deliveries because of insufficient battery energy.

Of course, it will be appreciated that the invention may take forms other than those specifically described. In addition, the values stated for the various components and relationships described above are merely representative, and those components or relationships may take on other values as suggested by the description and drawings. The scope of invention, however, is to be determined solely by the following claims.

What is claimed is:

1. A circuit for detecting an impending failure of a battery in an iontophoretic system comprising:

a microprocessor having an analog-to-digital (A/D) converter for converting an analog input to a digital output, said microprocessor capable of selecting between a voltage reference voltage $V_{ref}$ and a battery voltage $V_{cc}$ as a reference for the A/D converter, wherein when $V_{cc}$ is selected as the A/D reference, $V_{ref}$ is read by said A/D converter of said microprocessor as the analog input, the A/D converter outputting a digital count proportional to the ratio ($V_{ref}/V_{cc}$), wherein the impending failure of the battery is determined when the digital count is greater than a predetermined threshold.

* * * * *

UNITED STATES PATENT AND TRADEMARK OFFICE
CERTIFICATE OF CORRECTION

PATENT NO.       : 6,678,555 B2
APPLICATION NO.  : 10/127333
DATED            : January 13, 2004
INVENTOR(S)      : Flower et al.

Page 1 of 1

It is certified that error appears in the above-identified patent and that said Letters Patent is hereby corrected as shown below:

Column 2, line 1, delete "charge" and substitute therefor --charged--.

Column 5, line 67, delete "can not" and substitute therefor --cannot--.

Column 6, line 49, delete "soft ware" and substitute therefor --software--.

Column 6, line 49, delete "instrictions" and substitute therefor --instructions--.

Column 6, line 63, insert --to-- in between microprocessor and reset.

Column 10, line 1, delete first occurrence of "voltage".

Signed and Sealed this

Twenty-eighth Day of October, 2008

JON W. DUDAS
*Director of the United States Patent and Trademark Office*